United States Patent [19]

Suzuki

[11] Patent Number: 4,462,397
[45] Date of Patent: Jul. 31, 1984

[54] BREATHING CIRCUIT
[75] Inventor: Tatsuo Suzuki, Yokohama, Japan
[73] Assignee: Terumo Corporation, Tokyo, Japan
[21] Appl. No.: 364,204
[22] Filed: Apr. 1, 1982
[30] Foreign Application Priority Data Apr. 3, 1981 [JP] Japan .................................. 56-49278
May 18, 1981 [JP] Japan ............................ 56-71676[U]

[51] Int. Cl.³ ........................................... A61M 16/00
[52] U.S. Cl. .............................. 128/200.14; 128/911; 128/200.18
[58] Field of Search ............... 128/911, 200.14, 200.18

[56] References Cited
U.S. PATENT DOCUMENTS 3,826,255 7/1974 Havstad .
3,874,379 4/1975 Enfield et al. .................. 128/200.18
3,945,378 3/1976 Paluch ............................ 128/200.18

FOREIGN PATENT DOCUMENTS 54-150893 11/1979 Japan .
2029703 3/1980 United Kingdom .

Primary Examiner—Henry J. Recla

Attorney, Agent, or Firm—Frishauf, Holtz, Goodman & Woodward

[57] ABSTRACT

A breathing circuit includes a double-wall coaxial main tube comprising a flexible inner tube forming an inhalation path and a corrugated outer tube disposed outside said inner tube and defining an exhalation path in conjunction with said inner tube; and a manifold including two sets of coaxially disposed inner and outer manifold tubes positioned along the length of the coaxial main tube and connected to corresponding tubes of the main tube. The manifold being provided with (a) a nebulizer which closes off confronting ends of connected sections of the outer tube in an axial direction and communicates with inner spaces of connected sections of the inner tube of the coaxial main tube, (b) a bypass interconnecting the exhalation path of the two outer tube sections which are closed and separated by the nebulizer, and (c) an exhalation valve provided in the bypass path and including a valve body capable of closing the bypass during inhalation. An inner tube retaining member is provided at the patient end of the coaxial main tube for fixing the inner tube and the outer tube and maintaining the inner and outer tubes at a fixed distance radially from each other.

22 Claims, 10 Drawing Figures

BREATHING CIRCUIT

BACKGROUND OF THE INVENTION

1. Field of the Invention

This invention relates to a breathing circuit. More particularly this invention relates to a coaxial breathing circuit in a respiratory therapy device.

2. Description of Prior Arts

Of the breathing circuits heretofore introduced for use in the administration of ventilation, there are a wide variety of the type to be used by connecting them to ventilators (otherwise called "respirators").

Conventional devices of the class mentioned above generally have been constructed so that an inhalation tube adapted to feed the patient with air or an oxygen-rich gas mixture in a compressed state via a ventilator through, or not through, a heated humidifier, and an exhalation tube adapted to release the gas exhaled by the patient into the ambient air either directly or indirectly via a ventilator or spirometer, are formed of two separate tubes except for a Y-piece serving as a mouthpiece.

The presence of an inhalation tube and an exhalation tube in a mutually separated form between the ventilator and the patient, however, causes an inconvenience in the handling of the device, adds to the complexity of medical equipment used on the patient undergoing the administration of ventilation and appended by a number of transfusion lines and monitor lines connected to the patient's body and, during a bronchial lavage, offers possible interference and even hindrance. To preclude the difficulties mentioned above, there has been suggested a breathing circuit wherein the inhalation and exhalation tubes are formed with a coaxial tube consisting of an external tube and an internal tube and, therefore, appear to be one tube (Japanese Published Unexamined Patent Application No. 150,893/1979). This circuit comprises a coaxial tube formed by coaxially arranging a straight inner tube and a usually corrugated outer tube, with the interior of the inner tube used for passage of the inhalation and the space between the outer tube and the inner tube used for passage of the exhalation. The patient side end of the outer tube is fastened to a connector provided with an opening for the passage of both incoming and outgoing air, and the inner tube is positioned near this air opening. The other ends of the outer tube and inner tube on an anaesthetic machine side are respectively fitted to a manifold, so that the anaesthetic machine will feed in and out the air via the orifices of this manifold which respectively communicate with the inner tube and the outer tube.

Such formation of the inhalation and exhalation tubes in a coaxial construction for use in the ventilator or anaesthetic machine offers the advantage that the handling of the device becomes easy. The use of the corrugated tube as an outer tube, however, is inevitably required in order for the passage to be prevented from an otherwise possible crush due to the so-called kinking. When the pressure is applied to the interior of the passage during the inhalation, the outer tube is consequently expanded mainly in its axial direction by this pressure. The end of the inner tube which falls on the patient side of the circuit is not fastened generally to the connector to which the outer tube is fixed. Consequently, the entire circuit is expanded by the rise of the inner pressure inevitably to increase the variation of the mechanical dead space.

When the circuit of this nature is used as a respiration circuit, there is a possibility that the increase and decrease of the mechanical dead space based on the overall elongation of the circuit will vary the amount of ventilation and keep it from reaching the expected level in accordance with increase and decrease of the inner pressure of the circuit, based on variation of air passage. There is entailed another disadvantage that throughout the course of the ventilation, the ventilator should be kept controlled for the adjustment of the amount of ventilation. When the aforementioned coaxial tube is put to use, it can be adapted for the ventilator if the ventilator itself is of the type incorporating therein necessary devices such as the exhalation valve. Otherwise, the adaptation is not obtained. This point forms a problem for the circuit under discussion.

Further, Japanese Published Unexamined Patent Application No. 150,893/1979 discloses an embodiment in which the inner tube is free in its axial direction at the connector on the patient side. In this construction, however, the inner tube is separated from the spacer and the whole circuit is expanded when the inner pressure is raised to a level over some tens of cm $H_2O$ owing to the increase of the airway resistance and/or of the lung compliance. This embodiment has been demonstrated to be incapable of precluding the disadvantages mentioned above.

Generally in the administration of artificial respiration, it becomes necessary to dose aerosolized or a medication for the purpose of humidifying the inhalation, decreasing the viscosity of sputum in the patient's airway, or dilating the bronchus. Sometimes, therefore, a nebulizer (atomizer) is incorporated in the inhalation tube. In this case, to retain the efficiency of airsol inhalation intact and keep the patient from extra burden, the nebulizer is desired to be disposed at a position halfway in the length of the inhalation path and relatively close to the patient side. It is difficult, however, to insert the nebulizer only in the inhalation path of the coaxial circuit. No case has been known to the art in which the nebulizer is successfully inserted in the coaxial circuit of the construction described wherein above the product thus obtained is effectively used as a breathing circuit.

As a breathing circuit adaptable for a system which provides no exhalation valve for the ventilator as described above, there has been already proposed a manifold designed to provide the nebulizer and the exhalation valve in the exhalation tube (U.S. Pat. No. 3,826,255). Because of its particular construction, however, this manifold is intended for use with a breathing circuit containing two single-wall tubes instead of the coaxial tube. Thus, it cannot be adapted for the coaxial breathing circuit which enjoys the convenience of handling as described above. The applications found for the conventional coaxial tube breathing circuit have been limited.

British Patent Publication No. 2,029,703 discloses an anestherizing circuit which has both an inner and an outer tube fastened to the patient side connector. In this specification, the desirability of using corrugated tubes for both the inner and the outer tube is mentioned. It has been found that, when the circuit disclosed in this specification as exclusively designed for anesthetic is adopted as a breathing circuit, the use of corrugated tubes for the inner and the outer tube brings about rather undesirable results. The breathing circuit, by nature, is used for a much longer period than an anesthetizing circuit. Consequently, the inner pressure of the circuit is heightened as by the increase in the resistance of the airway and change of lung compliance, with the result that the whole circuit is expanded and the mechanical dead space is increased. Besides, the change in the resistance of the airway causes the volume of dead space to vary with elapse of time. In this case, since the inner tube restricts the expansion of the outer tube, the volume of the dead space is smaller than when the inner tube is not fixed to the patient side connector. It is nevertheless difficult to maintain the volume of ventilation constantly, because there is still the dead space change based on elongation of the corrugated tube itself. Since the circuit is primarily intended for the anesthetic circuit, the insertion of a nebulizer in the circuit is indicated or suggested nowhere in the specification of the British patent publication.

An object of the present invention, therefore, is to provide a novel breathing circuit.

Another object of the invention is to provide a coaxial breathing circuit which reduces the expansion and contraction of the entire circuit and the change of volume of the dead space to extremely small extents even when the inner pressure of the circuit extremely rises, and which limits to an extremely small extent the time-course variation of the volume of dead space due to the change in the resistance of the airway.

A further object of the invention is to provide a coaxial breathing circuit which is provided with a nebulizer and an exhalation valve.

SUMMARY OF THE INVENTION

The objects described above are accomplished by a breathing circuit comprising in combination (A) a coaxial main tube comprising a flexible inner tube forming an inhalation path and a corrugated outer tube disposed outside the inner tube and defining an exhalation path in conjunction with the inner tube; (B) manifold formed of a coaxially disposed inner and outer tubes positioned midway along the length of the coaxial main tube and connected to the main tube, the manifold being provided with (a) a neubulizer closing a path of the outer tube in an axial direction and communicating with inner spaces of one and the other inner tube of the coaxial tube, (b) a bypass interconnecting the exhalation path of the two outer tubes closed and separated by the nebulizer, and (c) an exhalation valve provided midway along the bypass and having a valve body capable of closing the bypass during inhalation, and (C) an inner tube retaining member provided at an outlet side end of inhalation of the coaxial main tube for fixing the inner tube and the outer tube and adapted to keep the inner and outer tube at a fixed distance from each other.

PREFERRED EMBODIMENT OF THE INVENTION

Figure 1:
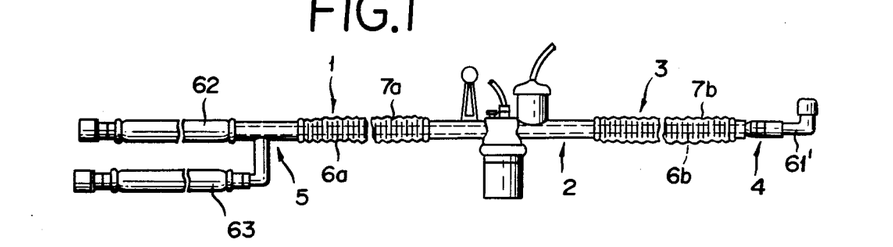
FIG. 1 is a side view of the construction of a coaxial breathing circuit according to the present invention.

As illustrated in FIG. 1, the breathing circuit contemplated by this invention essentially comprises a first coaxial main tube 1, a coaxial manifold 2, a second coaxial main tube 3, and an inner tube retaining member 4 serially interconnected in the order mentioned. Optionally, the first coaxial type main tube 1 is connected to a forked pipe 5.

The first and second coaxial main tubes 1, 3 are formed respectively of flexible inner tubes 6a, 6b each constituting an inhalation path, and corrugated outer tubes 7a, 7b coaxially disposed outside the inner tube and defining exhalation paths in conjunction with the respective inner tubes. The inner tubes 6a, 6b generally are straight or corrugated flexible tubes having a circular cross section. Particularly, straight flexible tubes are desirable because they permit less expansion of the circuit. The outer tubes 7a, 7b generally are corrugated flexible tubes having a circular cross section. The corrugated outer tubes serve to lessen the possible crush of the circuit.

In no other respect are the inner and outer tubes of the coaxial main tubes limited, providing that under normal conditions, the two main tubes are substantially equal in length. The total of the lengths of the first and second coaxial main tubes 1, 3 is desired to be about 0.7 to 1.5 meters. The inside diameters of the inner and outer tubes may be respectively in the ranges of about 8 to 20 mm and about 20 to 32 mm. The ratio of the outside diameters may be in the range of about 1:1.5 to 1:2.5. The material for the inner tubes and that for the outer tubes may be or may not be identical. These tubes may be made of any known material available for the manufacture of flexible tubes. Examples of the material include polyethylene, polypropylene, polyurethane, ethylene-vinyl acetate copolymer, polyvinyl acetate, polyvinyl alcohol, polyamide, polyvinyl chloride and polyethylene terephthalate. The wall thickness of the inner tubes, that of the outer tubes, the sizes of corrugated tubes, etc. may be suitably selected within the condition normally accepted.

In the first and second coaxial type main tubes 1, 3 constructed as described above, the inner tubes 6a, 6b are used as inhalation paths and the spaces intervening between the inner tubes 6a, 6b and the outer tubes 7a, 7b are used as exhalation paths.

Figure 2:
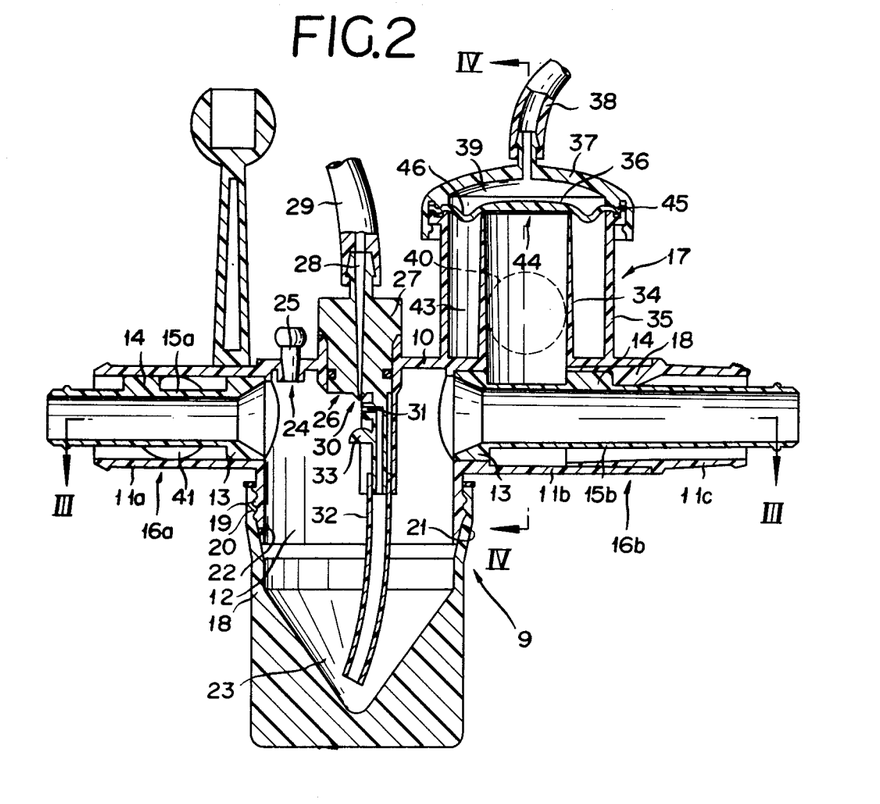
FIG. 2 is an enlarged longitudinal cross section of a coaxial manifold to be used in the breathing circuit according to the present invention.
Figure 3:
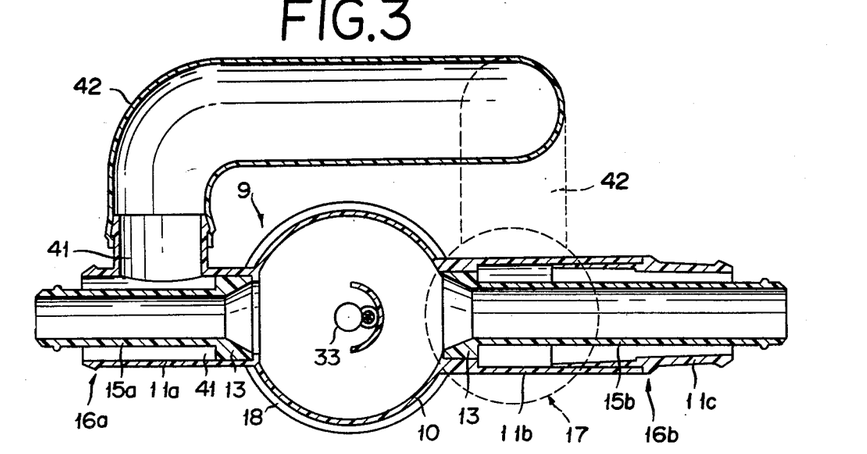
FIG. 3 is a cross section taken along the line III—III in the diagram of FIG. 2.
Figure 4:
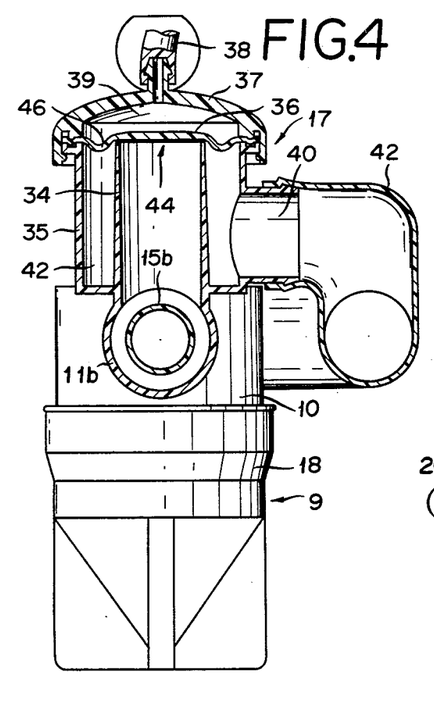
FIG. 4 is a cross section taken along the line IV—IV in the diagram of FIG. 2.

In the manifold 2, as illustrated in FIGS. 2 to 4, outer tubes 11a, 11b are projected from the lateral wall of a cap 10 of a nebulizer 9 and are allowed to communicate with a cavity 12 in the nebulizer. Inside the outer tubes 11a, 11b, inner tubes 15a, 15b provided at the inner ends thereof each with a flange 13, and near the outer ends thereof each with spacers projected outwardly from at least two positions, e.g. from three positions, relative to the axes of the outer tubes 11a, 11b and adapted to adjoin the inner walls of the outer tubes, are coaxially inserted in such a manner that the flanges 13 will come into contact with the lateral wall of the cap 10. Thus, the outer tubes 11a, 11b and the inner tubes 15a, 15b form coaxial tubes 16a, 16b. If the inner tubes 15a, 15b are held in the outer tubes 11a, 11b by the flanges 13 and spacer 14, they are extremely easier to produce than one which is molded integrally with the manifold 2. The spacers 14 are in the form of blades disposed, for example, parallel to the axial lines of the coaxial tubes. They may be in the form of columns or some other similar objects on condition that they should refrain from closing the exhalation paths to be formed between the outer tubes 11a, 11b and the inner tubes 15a, 15b. Optionally, in the outer tube 11b which is provided with an exhalation valve 17 described more fully later, an outer tube connector 11c having spacers 18 resembling the aforementioned spacers and projected inwardly radially relative to the axial line may be inserted when necessary. By the flanges 13 provided at the inner ends of the inner tubes 15a, 15b are described above, the exhalation paths formed between the outer tubes 11a, 11b and the inner tubes 15a, 15b are shut off by the nebulizer 9. The inner tubes 15a, 15b are allowed to communicate with the cavity in the nebulizer 9.

The nebulizer 9 may be formed integrally in a one-piece construction. Generally, it comprises a cap closing the inner ends of the outer tubes 11a, 11b of the manifold 2 comprising the coaxial tubes 16a, 16b and communicating with the inner ends of one inner tube 15a and the other inner tube 15b and a container 18 fitted freely detachably to the cap 10 as illustrated in FIG. 2. The connection between the cap 10 and the container 18 may be made in any of the forms available. Generally, it is accomplished by means of matched screws 19, 20. In particular, this connection is obtained desirably by providing the screw 19 at the portion of the cap 10 destined for contact with the container and a fitting part 21 of a tapered surface at the leading end of the screw 19, and also by providing the screw 20 at the portion of the container 18 destined for contact with the cap and a fitting part 22 of a tapered surface at the inner-most recess of the screw 20. The screws are formed in ample lengths such that as the cap 10 is helically advanced into the container 18, the respective fitting parts 21, 22 of tapered surface will be brought into intimate engagement with each other. The container 18 forms a reservoir 23 for a medication or water. The cap 10 is provided at the top thereof with a port 24 for the introduction of a medicinal solution. This port 24 is normally closed with a rubber stopper 25. In this case, even if the stopper is not removed, the medicinal solution can be introduced by inserting a needle of a syringe into a rubber portion, and thus contamination in the nebulizer by air can be prevented. Also at the top of the cap 10, a release nozzle port 26 is formed. The release nozzle port 26 is fitted with an O ring, for example, and permits insertion of an outer pressure release nozzle 27 which is provided at the lower portion thereof with a venturi mechanism. The inlet 28 to this nozzle 27 communicates with an outer pressure inlet tube 29. The lower end of this inlet 28 forms an outer pressure release outlet 30. Near the leading end of the release outlet 30 is disposed a medication spray nozzle 31. This nozzle 31 communicates with a tube 32. At a still lower portion of the aforementioned release outlet 30 is provided a baffle member 33.

Figure 5:
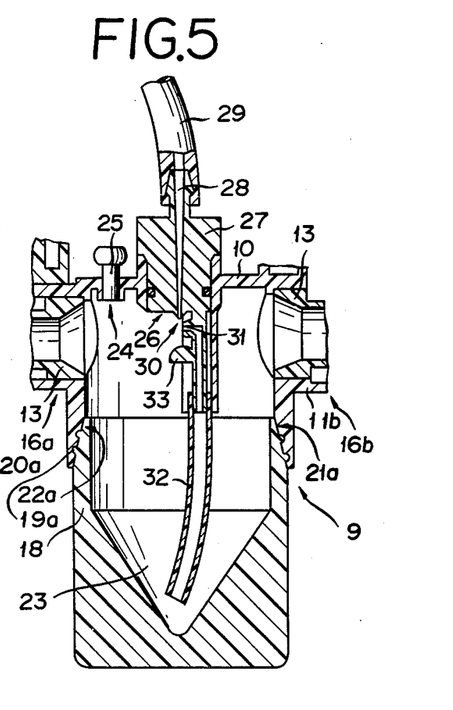
FIG. 5 is a cross section of another preferred embodiment of the nebulizer.
Figure 6:
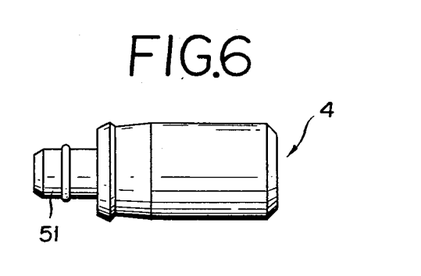
FIG. 6 is an enlarged side view of a connector.
Figure 7:
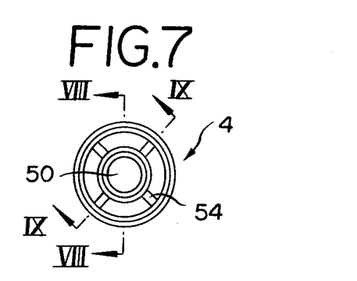
FIG. 7 is an enlarged front view of the connector.
Figure 8:
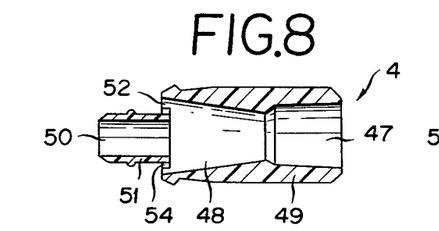
FIG. 8 is a cross section taken along the line VIII—VIII in the diagram of FIG. 7.
Figure 9:
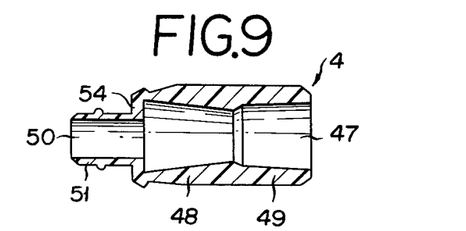
FIG. 9 is a cross section taken along the line IX—IX in the diagram of FIG. 7.

In the preferred embodiment of FIG. 2, the inner surface at the upper end of the container 18, is fitted on the outer surface at the lower end of the cap 10. For the purpose of this engagement, their respective fitting parts 21, 22 of tapered surface are formed below the respective screws 19, 20. Optionally, the screws 19, 20 and the fitting parts 21, 22 of tapered surface may change their places. FIG. 5 illustrates a typical example of such change of places. In this case, the outer surface at the upper end of the container 18 is fitted around the inner surface at the lower connecting part of the cap 10. To permit this engagement, therefore, the fitting parts 21a, 22a of tapered surface are formed in the upper portions of the screws 19a, 20a. In both cases, the fitting parts of tapered surface 21, 22 and 21a, 22a are required to be brought into safe, intimate contact with each other. This requirement is fulfilled by equalizing the angles of inclination of the tapered surfaces of the fitting parts 21a, 22a positioned inside (tapered surface 21 in the embodiment of FIG. 2 and tapered surface 22a in the embodiment of FIG. 5).

The exhalation valve 17 is disposed on the outer tube 11b, namely the one on the inhalation inlet (patient) side of the two outer tubes closed and separated from each other by the nebulizer 9 as illustrated in FIGS. 2 to 4. The exhalation valve 17 comprises an inner cylinder 34 disposed communicably with the outer tube 11b and an outer cylinder 35 disposed coaxially with the inner cylinder 34, not allowed to communicate with the outer tube 11b, and shut off to the ambient air. The open edges of the inner and outer cylinders 34, 35 are sealed tightly with a valve body, i.e., a diaphragm 36. This diaphragm 36 is fastened to the circumferential edge of the outer cylinder 35 by means of a cap 37. The cavity enclosed between the cap 37 and the diaphragm 36 communicates with the tube 38 and forms a compression chamber 39 to which is supplied an actuating pressure of the exhalation valve for closing the exhalation path by causing the positive end-expiratory pressure through the tube 38 to act upon the outer surface of the diaphragm 36 in case of inhalation. In the lateral wall of the outer tube 35, a port 40 opens. Also, a port 41 opens in the lateral wall of the other outer tube 11a which is closed by the nebulizer 9. These ports 40, 41 are interconnected by a bypass tube 42. The exhalation forwarded from the patient side as described more fully later, finds its way through the outer tube 11b to the inner cylinder 34 of the exhalation valve 17, pushes the diaphragm 36 upwardly, reaches the cavity 43 formed between the outer cylinder and the inner cylinder 34, and further advances through the port 40 of the outer cylinder 35, the by-pass tube 42, and the port 41 to the interior of the outer tube 11a. The above mentioned valve body is not limited to the diaphragm 36, but any member which closes the open edge of the inner cylinder to during inhalation, and opens it to during exhalation, can be used.

The manifold 2 containing the outer tube, the inner tube, the nebulizer, and the exhalation valve may be made of the same material as the coaxial type main tube. Otherwise, it may be made of polyacetal, an ABS resin, etc. The diaphragm 36 is made of natural rubber or synthetic rubber such as chloroprene rubber, SBR, silicone rubber, etc. for example.

In the exhalation valve 17, the cap 37 which fastens the diaphragm 36 to the upper edge of the outer cylinder 35 is fixed so as to cover the open edge 44 of the inner cylinder 34 and give rise to the compression chamber 39 on the diaphragm 36. In this case, the diaphragm 36 is fixed by having the periphery 45 thereof pinched between the outer cylinder 35 and the cap 37 in such a manner that the peripheral face of the inner cylinder of diaphragm 36 is separated by a gap of at least 0.2 mm, preferably 0.2 to 0.5 mm, from the open edge 44 of the inner cylinder, while the compression chamber 39 positioned thereon is free from pressure. The central portion of the diaphragm 36, namely the portion corresponding to the inner cylinder 34, has a wall thickness at least twice the wall thickness of the peripheral portion falling outside the inner cylinder 34. In the portion of the diaphragm falling outside the inner cylinder 34, an annular groove 46 is formed.

A baloon shaped valve body may be provided at the outlet of air for compression of the cap 37 instead of the diaphragm, which can close the open edge 44 of the inner cylinder 34 by expansion thereof.

At the leading end of the coaxial type main tube 3 connected to the coaxial tube 16b on the exhalation valve 17 side of the manifold 2, there is provided the inner tube retaining member 4 which serves to keep the inner tube 6b and the outer tube 7b at a fixed distance from each other. The inner tube retaining member 4 may be formed of protuberances which are raised radially relative to the axis of the inner tube 6b in a plurality of directions, three directions, for example, to the extent of substantially adjoining the inner surface of the outer tube. A connector 4 of the construction illustrated in FIGS. 6 through 9 is preferably used as the inner tube retaining member 4. The inner tube retaining member 4 is in the form of an outer tube portion 49 provided at one end thereof with an air hole 47 and at the other end thereof with an outer tube fitting end 48. Inside the outer tube fitting end 48, an inner tube fitting portion 51 provided with an inner tube fitting end 50 is coaxially disposed. Between the inner tube fitting portion 51 and the outer tube portion 49, a plurality of openings 52 are formed. Through the portions excluding these openings 52, the inner tube fitting portion 51 and the outer tube portion 49 are connected to each other. In other words, the inner tube fitting portion 51 is connected to the outer tube portion 49 with columnar pieces 54 projected outwardly at fixed intervals radially from the axial line. They are usually molded integrally in a one-piece construction. The openings 52 may be formed circularly, elliptically, or otherwise as freely selected. They are generally formed integrally with any of the synthetic resins mentioned above. The inner tube fitting portion 51 is generally made to protrude from the leading end of the outer tube fitting end 48 with a view to facilitating the fitting of the inner tube 6b and the outer tube 7b of the coaxial main tube 3.

To the outer tube 49 and the inner tube fitting member 51 of this inner tube retaining member 4, the outer tube 7b and the inner tube 6b are respectively fitted. The fitting is accomplished by simply inserting these tubes around the respective fitting ends and fastening the fitted end of the outer tube 7b with application of pressure to suit the occasion. It is because the outer tube 7b and the inner tube 6b are fastened to the inner tube retaining member 4 that the expansion of the whole circuit is decreased to an extremely small extent.

Figure 10:
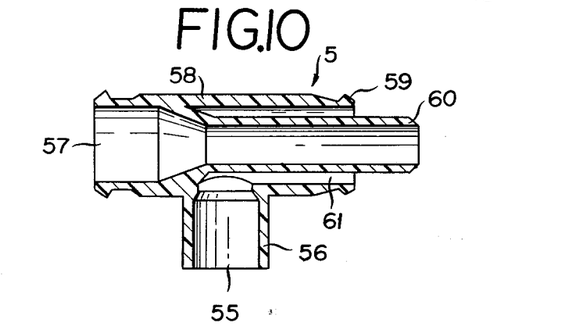
FIG. 10 is an enlarged cross section of a forked pipe.

The one end of the other circuit main tube 1 that is connected to the manifold 2 is connected to the forked pipe 5. The forked pipe 5 is provided with a side pipe 56 forming an outer tube communication hole 55, and a main pipe 58 forming an inner tube communication hole 57. The other end of the main pipe 58 forms an outer tube fitting member 59. Inside the outer tube fitting member 59, an inner tube fitting member 60 is coaxially disposed. One end of the inner tube fitting member 60 forms an opening and the other end thereof continues into the inner wall of the main pipe 58 to close the outer tube fitting member 59. All these components are integrally molded of any of the aforementioned synthetic resins. The outer tube communication hole 55 of the side pipe 56 communicates with a cavity 61 which is formed between the outer tube fitting member 59 and the inner tube fitting member 60. With the forked pipe 5 of the construction described above, the outer tube 7a and the inner tube 6a of the coaxial main tube 1 are fitted fast respectively to the outer tube fitting member 59 and the inner tube fitting member 60.

Now, the actual use to which the breathing circuit of this invention constructed as described above is put, will be described. As illustrated in FIG. 1, the first coaxial main tube 1, the coaxial manifold 2, the second coaxial type main tube 3 and the inner tube retaining member 4 are serially connected in the order mentioned. Optionally, the mouthpiece (L-shaped pipe) 61′ is connected to one end of the inner tube retaining member 4. Then, the forked pipe 5 is connected to one end of the first coaxial main tube 1. The inner tube communication hole 57 is connected to a ventilator (not shown) through the medium of the tube 62. The outer tube communication hole 55 is connected to a spirometer (not shown) through the medium of the tube 63.

A medicinal solution is supplied by inserting a needle of a syringe which contains the solution into the rubber stopper 25 and then injecting the solution. The mouthpiece 61 is applied to the patient. Subsequently, the ventilator is actuated to supply the inhalation gas through the tube 62, the inner tube communication hole 57 of the forked pipe 5, and the inner tube 6a of the first coaxial main tube 1 into the inner tube 15a of the manifold 2, and further into the nebulizer 9. Through the tube 29, external pressure is led into the outer pressure release nozzle 27, and intermittently released through the release outlet 30. By the negative pressure of the jet of air loaded to the outlet of the spray nozzle 31, the medicinal solution is sucked up through the tube 32 and atomized in the form of aerosol owing to the so-called venturi effect. Since the baffle member 33 is disposed in the direction in which the jet of air is spurted, the atomized medicinal solution now carried on the jet is thrust violently against the baffle member 33 and consequently is scattered. The particle diameter of the individual particles of the aerosol, therefore, is all the more uniformized. The same gas as one supplied to the patient is generally used as the source for the jet supplied through the release outlet 30. The release of this jet of air is intermittently performed so that the jet is fed in only during the inhalation. Optionally, the medicinal solution may be supplied through the medicinal solution supply port 24 after removing rubber mounting stopper 25.

The inhalation gas mixed with the aerosol in the nebulizer 9 is forwarded through the interior of the inner tube 15b of the manifold, the inner tube 6b of the second coaxial main tube 3, the inner tube retaining member 4, and the mouthpiece 61′ to the endo-tracheal tube, for example, on the patient (not shown) side to effect desired administration of ventilation. If administration of the medicinal solution is not necessary, the ventilation can, of course, be administered through a similar inhalation path without introducing outer pressure.

The exhalation gas discharged from the patient advances through the mouthpiece 61′, the inner piece retaining member 4, the opening 52 of the inner piece retaining member 4, the exhalation path formed in the cavity between the outer tube 7b and the inner tube 6b of the second coaxial main tube 3, and the cavity between the outer tube 11b and the inner tube 15b of the manifold 2 into the inner tube 34 of the exhalation valve 17.

Within the exhalation valve 17, air of relatively high pressure is supplied through the tube 38 into the compression chamber 39 to keep the diaphragm 36 pressed against the opening edge 44 of the inner cylinder and close tightly the flow path of the inner cylinder 34, when inhalation is administered. Thus an O ring for sealing is not necessary. During the interval of exhalation which follows the completion of the supply of the inhalation gas, the exhalation gas pushes the diaphragm 36 up, flows into the cavity 43 formed between the outer cylinder 35 and the inner cylinder 34 on account of release of pressure in the compression chamber 39, advances from the outer cylinder 35 through the bypass path 42 to the cavity formed between the outer tube 11a and the inner tube 15a of the manifold 2, passes through the exhalation path formed between the outer tube 7a and the inner tube 6a of the first coaxial main tube 1, and reaches the spirometer or ventilator (not shown) or the ambient air via the forked pipe 5. Further, the annular groove 46 is provided at a portion out of the inner cylinder in the diaphragm 36, so a larger gap is formed between the open edge of inner cylinder and the diaphragm by elongation of the annular groove 46 when the diaphragm 36 lifts up during inhalation, and it gives good efficiency when exhalation gas is exhausted.

During the flow of the exhalation gas, the air pressure applied through the tube 38 to the compression chamber 39 on the diaphragm 36 of the exhalation valve 17 is reduced to a great extent and, consequently, the exhalation gas is allowed to push up the diaphragm 36 from inside the inner cylinder 34 and flow into the cavity 43 outside the inner cylinder 34. Further, positive end-expiratory pressure treatment is carried out, if desired, the air pressure applied to the interior of the compression chamber 39 is not completely released but is allowed to exert slight positive pressure enough not to allow the inner pressure of the lungs of the patient to drop to 0 cm $H_2O$ at the end of exhalation, e.g., allowing 5 cm $H_2O$. It goes without saying that in the case of a patient to whom the positive end-expiratory pressure need not be applied at the end of the exhalation, the air pressure within the compression chamber 39 can be adjusted to 0.

The following experiment was carried out with a view to confirming the effect of the present invention.
Experiment:

Two corrugated tubes of polyethylene 0.5 m is length were prepared to serve as outer tubes 7a, 7b for the coaxial main tubes 1, 3. These corrugated tubes had a wall thickness of 0.75 mm, outside diameters of 23.5 mm at the grooves and 27.5 mm at the ridges. Two straight tubes of polyvinyl chloride 0.5 m in length, 11 mm in inside diameter, and 0.75 mm in wall thickness were prepared to serve as inner tubes 6a, 6b. A breathing circuit constructed as shown in FIG. 1 was formed with these outer tubes 7a, 7b and inner tubes 6a, 6b, and was used as Circuit A.

Two corrugated tubes of polyvinyl chloride 0.5 m in length, 0.75 mm in wall thickness, 10.5 mm in outside diameter at grooves, and 14.5 mm in outside diameter at ridges, and two corrugated tubes of polyethylene 0.5 m in length, 0.75 mm in wall thickness, 23.5 mm in outside diameter at grooves, and 27.5 mm in outside diameter at ridges, were prepared to serve as inner tubes 6a, 6b and outer tubes 7a, 7b respectively. Another breathing circuit of the construction of FIG. 1 was formed with these tubes. It was used as Circuit B.

For the purpose of comparison, a breathing circuit similar to Circuit A mentioned above was formed by using the aforementioned straight tubes as inner tubes and the aforementioned corrugated tubes as outer tubes and maintaining the inner tubes slidably in an axial direction to the inner piece retaining member 4 with spacers instead of providing an inner tube fitting member 51 for the inner piece retaining member 4. This circuit was used as Circuit C.

In the three circuits described above, a pressure of 60 cm $H_2O$ was applied to the inner tubes 6a, 6b and, during the presence of this load, the inner tubes were tested for expansion. The results were as shown in Table 1.

TABLE 1

| Circuit | Inner tube | Ratio of expansion (%) |
|---------|------------|------------------------|
| A | Straight tubes | 0 |
| B | Corrugated tubes | 9 |
| C | Straight tubes | 15 |

It is noted from Table 1 that circuits were expanded to a great extent when corrugated tubes were used as inner tubes 6a, 6b and when the inner tube 6b was not fixed to the inner tube fitting member 51. In circuit C, the inner tube 6b came off the connector 4 by retreating. Further, the experiments were carried out by varying the materials of the inner and outer tubes to obtain similar results.

In the breathing circuit of this invention, the manifold 2 which is formed in a coaxial construction and provided in paths thereof with the nebulizer 9 for closing the outer tubes and communicating with the inner tubes, and with the exhalation valve 17 communicating with the outer tubes, is interposed between the coaxial main tubes 1, 3. Owing to this particular construction, therefore, this breathing circuit can be easily adapted for a ventilator of the type not incorporating any exhalation valve without sacrificing simplicity, an inherent merit of a double-wall breathing circuit, by merely joining the exhalation valve 17 to the exhalation path and the nebulizer 9 to the inhalation path, respectively. Besides, the breathing circuit can be handled very simply. The present invention, accordingly, has the advantage that the adaptability of highly beneficial coaxial breathing circuits will be expanded to a wide variety of types of ventilators.

Further, the coaxial manifold 2 which is provided in the coaxial breathing circuit permits the nebulizer 9 and the exhalation valve 17 to be integrally incorporated in the coaxially disposed inner and outer tubes 6a, 6b and 7a, 7b, respectively. The warmth of prewarmed inhalation gas flowing inside the inner tubes 6a, 6b is maintained by the warm exhalation gas freshly discharged from the patient's body and forwarded through the outer tubes 7a, 7b. This invention, therefore, manifests an effect of efficiently utilizing the functions of the nebulizer and the exhalation valve without jeopardizing the essential significance of a coaxial breathing circuit.

Moreover, since the coaxial manifold 2 has the inner tubes 6a, 6b for passing the inhalation gas and the outer tubes for passing the exhalation gas integrally formed in a one-piece two-wall coaxial construction as described above, it enjoys the advantage that the insertion of the manifold 2 between the two coaxial main tubes 1, 3 can be effected by a very simple procedure. Since the nebulizer 9 is disposed in such a manner that the cap 10 will intervene between the outer tubes 7a, 7b and keep them closed and communicate with the inner tubes 6a, 6b, it can be fixed in position relative to the inner tubes 6a, 6b. Since the exhalation valve 17 is disposed in such a manner as to communicate with the outer tubes 7b, i.e. the patient side tube of the outer tubes 7a, 7b is closed by the nebulizer 9, it can be fixed in position relative to the outer tube. Further, since the outer cylinder 35 of the exhalation valve 17 and the outer tube 7a, i.e. the ventilator side tube of the outer tubes is closed by the nebulizer 9, are interconnected via the bypass path 42, the outer tube flow path can be ideally formed in the coaxial manifold 2, and the function of forwarding the current of the exhalation gas discharged from the patient's body through the shortest possible path along the periphery of the inner tubes without impairing the retention of warmth of the inhalation gas flowing through the inner tubes by exhalation, can be fully realized.

Moreover, in the coaxial manifold 2, since the nebulizer 9 is disposed so as to enable the cap 10 to intervene between the outer tubes 11a, 11b and close them and communicate with the inner tubes 15a, 15b, and since the container 18 as a reservoir for a medicinal solution, for example is freely detachably disposed at the lower end of the cap 10, it follows that the removal of the container 18 for washing after use can be easily effected. In this case, the portions of the cap 10 and the container 18 destined for mutual engagement are provided with the screws 19, 20 and further with the fitting parts of tapered surfaces 20, 21 as described above. As compared with the conventional airtight means which solely resorts to interposition of a packing device such as an O ring, the engagement of the cap 10 and the container 18 can be broken without entailing the possibility that an O ring will come off, deviate from its exact position, or fail to resume its correct position. Thus, there is derived an advantage that the attachment and the detachment of the container 18 can be easily carried out without impairing maximum airtightness of the manifold 2.

In the exhalation valve 17, the diaphragm 36 is set in position so that the rear surface thereof is separated by a small gap from the open edge 44 of the inner cylinder, and the portion of this diaphragm 36 serving to open and close the inner cylinder 34 is given a wall thickness greater than the wall thickness of the outer peripheral portion thereof. Consequently, on otherwise possible vibration of the diaphragm 36 during the passage of the exhalation gas in the presence of the positive end-expiratory pressure, can be precluded without fail. The smooth flow of the exhalation gas, therefore, can be ensured.

In the exhalation valve as used in the breathing circuit of the type of interest, it has been customary for the diaphragm to be positioned substantially flush with the open edge of the inner cylinder so that the diaphragm, in the absence of pressure, will come into tight contact with the open edge of the inner cylinder. If, in this case, a gas of high initial pressure flows in through the inner cylinder, the diaphragm is pushed up despite the positive end-expiratory pressure and the exhalation gas is allowed to escape from within the inner cylinder. When the pressure of the exhalation gas falls below the level of the aforementioned initial pressure, the end gas pushes up the diaphragm despite the positive end-expiratory pressure. The force with which the gas pushes up the diaphragm is weak and, thus, falls short of opening the diaphragm as required. When the diaphragm is placed flush with the open edge of the inner cylinder as described above, the diaphragm and the open edge of the inner cylinder approach very near to each other, and the upward pressure of the exhalation gas and the positive end-expiratory pressure applied downwardly are out of balance. Besides, the diaphragm on the inner cylinder has a small wall thickness. Under these conditions, the diaphragm inevitably generates vibrations. When the exhalation gas assumes the final gas pressure and falls below the level of the positive end-expiratory pressure, the diaphragm completely closes the open edge of the inner cylinder and shuts off the flow of the exhalation gas. The vibrations which are generated by the diaphragm during the exertion of resistance to the exhalation gas do not bring about any desirable effect upon the patient's exhalation, and they are sometimes felt as unpleasantness by noise.

When the diaphragm 36 is so positioned that, in the absence of pressure, the rear surface of the diaphragm is separated by a gap (desirably at least 0.2 mm, preferably 0.2 to 0.5 mm) from the open edge 44 of the inner cylinder and/or the portion of the diaphragm 36 corresponding to the inner cylinder 34 is given a wall thickness greater (preferably at least twice) than the will thickness of the outer peripheral portion thereof for the purpose of precluding the problem mentioned above, as in the exhalation valve 17 used in the present invention, the occurrence of vibrations of the diaphragm can be prevented without fail. In the exhalation valve of this construction, the diaphragm 36 is held tightly against the open edge 44 of te inner cylinder by the positive end-expiratory pressure under the condition preceding the start of the exhalation. As the initial gas pressure of the exhalation rises up the interior of the inner cylinder 34, the diaphragm 36 is pushed up and caused to release the gas from within the inner cylinder 34. As the exhalation gas is enervated to the point of assuming the final gas pressure, although the gas pressure is capable of pushing up the diaphragm 36 is spite of the positive end-expiratory pressure, the force of this upward push is short of positively cancelling the positive end-expiratory pressure. The diaphragm 36, consequently, is retained in its original position such that the rear surface thereof will remain out of contact with the open edge 44 of the inner cylinder. Owing to the fact that in the condition mentioned above, the gap of about 0.2 mm intervenes between the open edge 44 of the inner cylinder and the diaphragm 36 and the condition that the diaphragm itself has a greater wall thickness in the central portion thereof, the flow of the end gas pressure is allowed but, during the flow of this pressure, the diaphragm 36 is not caused to generate vibrations. When the exhalation assumes the final gas pressure and falls below the level of the positive end-expiratory pressure, the diaphragm 36 is caused by the positive end-expiratory pressure to close the open edge 44 of the inner cylinder and shut off the flow of the exhalation gas.

What is claimed is:
1. A breathing circuit, comprising:
  A. a coaxial main tube of given length having a patient side end and a ventilator side end, said main tube comprising first and second flexible inner tube sections for forming an inhalation path, and first and second corrugated outer tube sections disposed outside and coaxial with corresponding ones of said inner tube sections for defining an exhalation path between the inner peripheries of said outer tube sections and the outer peripheries of said inner tube sections;

B. a manifold including coaxially disposed first and second inner and first and second outer manifold tube sections each having opposite ends connected, respectively, to an end of a corresponding one of said flexible inner tube sections and said corrugated outer tube sections of said coaxial main tube, wherein said manifold is positioned medially along the length of said coaxial main tube, said manifold also including (a) a nebulizer arranged for communication with the interior of said first and said second inner manifold tube sections and wherein a part of said nebulizer closes confronting ends of said first and said second outer manifold tube sections in the axial direction of said coaxial main tube, (b) a tubular bypass interconnecting said exhalation path between said first and said second outer manifold tube tube sections, and (c) exhalation valve means provided in the path of the bypass for closing the bypass path during an inhalation through said inhalation path, wherein the exhalation valve means comprises an inner cylinder having one end connected to and fluidically communicating with an end portion of one of said first and said second outer manifold tube sections in the region of the end of the outer manifold tube section which is closed by the nebulizer part, an outer cylinder formed coaxially with said inner cylinder and having one end connected to said outer manifold tube section to form a space bound by the inner wall of the outer cylinder, the outer wall of the inner cylinder and the outer manifold tube section for receiving an exhalation from said end portion of the outer manifold tube sections, said inner cylinder having an opposite end defining a valve seat, said outer cylinder having an opposite end provided with valve closure means adapted to cooperate with said valve seat to control exhalation flow from within said inner cylinder into said space, said bypass including conduit means for fluidically communicating said space with the interior of an end portion of the other of said first and second outer manifold tube sections in the region of the end of the manifold outer tube section which is closed by the nebulizer part, and C. an inner tube retaining member provided at the patient side end of said coaxial main tube for fixing the corresponding inner tube section and the corresponding outer tube section and adapted to maintain the inner and outer tube sections at a fixed distance radially from each other.

2. A breathing circuit according to claim 1, wherein the flexible inner tube sections in the coaxial main tube are each in the form of a corrugated tube.

3. A breathing circuit according to claim 1, wherein the flexible inner tube sections of the coaxial main tube are each in the form of a straight tube.

4. A breathing circuit according to claim 1, wherein the inner tube retaining member comprises an outer tube mounting portion forming an air hole in the axial direction, an inner tube mounting portion formed coaxially with said outer tube mounting portion and defining at least one opening formed between said outer tube and said inner tube mounting portions in communication with said air hole, and portions adjacent said at least one opening for interconnecting said outer tube mounting portion and said inner tube mounting portion.

5. A breathing circuit according to claim 4, wherein the inner tube retaining member is formed so that said inner tube mounting portion outwardly protudes from said outer tube mounting portion at one end thereof.

6. A breathing circuit according to claim 4, wherein said inner tube retaining member has a plurality of openings formed at substantially equal intervals circumferentially between the inner tube and the outer tube retaining members.

7. A breathing circuit according to claim 6, wherein said openings have a circular shape.

8. A breathing circuit according to claim 6, wherein said portions interposed between the openings are in the shape of columns.

9. A breathing circuit according to claim 1, wherein said nebulizer comprises a generally cylindrical cap the lateral wall of which is arranged to support the inner and the outer manifold tubes and to close adjacent ends of the outer manifold tubes and for communicating with adjacent ends of the inner manifold tubes, and including a liquid container arranged to be detachably mounted to said cap to introduce liquid into the inhalation path.

10. A breathing circuit according to claim 9, wherein a portion of said cap destined for engagement with said container in the nebulizer is provided with a screw and the portion past the leading end of said screw is provided with a fitting part of tapered surface, and the portion of the container designed for engagement with the cap is provided with a screw and a fitting part of tapered surface matched to said cap screw and fitting part, respectively.

11. A breathing circuit according to claim 1, wherein said valve closure means of the exhalation valve has a peripheral portion fastened to said outer cylinder and is adapted to come into contact freely with said valve seat.

12. A breathing circuit according to claim 11, wherein the valve closure means is a diaphragm.

13. A breathing circuit according to claim 12, including a valve cap for sealingly engaging a circumferential edge of the outer cylinder of the exhalation valve means, wherein the diaphragm is fixed between said edge of the outer cylinder and the peripheral portion of the valve cap, wherein the valve cap forms a compression chamber in conjunction with said diaphragm.

14. A breathing circuit according to claim 13, wherein the diaphragm is fixed in position such that the inner cylinder side surface thereof is separated by a gap of at least 0.2 mm from said valve seat while the interior of the compression chamber is unpressurized.

15. A breathing circuit according to claim 13, wherein the portion of the diaphragm corresponding to said inner cylinder is given a wall thickness greater than the wall thickness of the outer peripheral portion thereof.

16. A breathing circuit according to claim 15, wherein the wall thickness of the portion of the diaphragm corresponding to the inner cylinder is at least twice that of the outer peripheral portion thereof.

17. A breathing circuit according to claim 15, wherein the portion of the diaphragm falling outside the inner cylinder is provided with an annular groove.

18. A breathing circuit according to claim 1, including a forked pipe for communicating with an inhalation gas source and an exhalation discharge part, and wherein the ventilator side end of the coaxial main tube is connected to said forked pipe.

19. A breathing circuit according to claim 18, wherein the forked pipe comprises an inner tube for communicating with the inhalation gas source and an outer tube formed coaxially with said inner tube and having one end thereof connected to said inner tube to be closed at said one end, and said outer tube is provided with a communication hole communicating with the exhalation discharge part.

20. A breathing circuit according to claim 19, wherein the inner tube of the forked pipe protrudes axially outwardly from the open end of the outer tube.

21. A breathing circuit according to claim 1, wherein each of the inner manifold tubes is formed with an end flange extending radially adjacent a side of the nebulizer, and the path of the outer manifold tubes is closed by said flanges inside said outer manifold tubes and the inner manifold tubes communicate with the interior of the nebulizer.

22. A breathing circuit according to claim 21, wherein each of the inner manifold tubes are retained in position within the outer manifold tubes by the flange provided at one end and each of the inner manifold tubes includes at least two spacers projecting radially outward near the other end thereof for contacting the inner wall of a corresponding outer manifold tube.

* * * * *